US011254964B1

(12) United States Patent
Stettler et al.

(10) Patent No.: US 11,254,964 B1
(45) Date of Patent: Feb. 22, 2022

(54) CELL CULTURE METHODS FOR INCREASED CELL VIABILITY

(71) Applicant: FRESENIUS KABI DEUTSCHLAND GMBH, Bad Homburg (DE)

(72) Inventors: Matthieu Stettler, Vucherens (CH); Hervé Broly, Chatel-St Denis (CH); Thomas Solacroup, Blonay (CH); Yolande Rouiller, Lausanne (CH)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 47 days.

(21) Appl. No.: 15/457,579

(22) Filed: Mar. 13, 2017

Related U.S. Application Data

(60) Provisional application No. 62/308,612, filed on Mar. 15, 2016.

(51) Int. Cl.
| | |
|---|---|
| *C07K 16/14* | (2006.01) |
| *C12P 21/02* | (2006.01) |
| *C07K 16/24* | (2006.01) |

(52) U.S. Cl.
CPC ............ *C12P 21/02* (2013.01); *C07K 16/241* (2013.01); *C07K 2317/14* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 7,294,481 B1 * | 11/2007 | Fung ................... | C07K 14/525 435/235.1 |
| 2015/0267237 A1 * | 9/2015 | Meier .................. | C07K 16/00 424/143.1 |
| 2019/0002822 A1 * | 1/2019 | Vijayasankaran ... | C12N 5/0018 |

FOREIGN PATENT DOCUMENTS

| | | | |
|---|---|---|---|
| WO | WO 9622792 | * | 8/1996 |
| WO | WO 2016110227 | * | 7/2016 |
| WO | WO2016153191 | * | 9/2016 |

* cited by examiner

*Primary Examiner* — Michail A Belyavskyi
(74) *Attorney, Agent, or Firm* — Fox Rothschild LLP

(57) ABSTRACT

The present invention relates to a method of maintaining cell viability at a level of at least 80% for up to 14 days in a fed-batch culture of cells producing a recombinant protein, the method comprising maintaining the cell culture medium at a pH of 6.5 to 7.0 and at a temperature of 31° C. to 35° C. for at least 5 consecutive days of the duration of the cell culture method.

13 Claims, 10 Drawing Sheets

Specification includes a Sequence Listing.

US 11,254,964 B1

CELL CULTURE METHODS FOR INCREASED CELL VIABILITY

BACKGROUND OF THE INVENTION

Recombinant proteins can be produced in amounts which allow for their use in many applications including therapeutic, diagnostic, agricultural and research purposes. In order for recombinant proteins to be used in such ways, they must be produced in sufficient amounts in an efficient and effective way. One way of increasing recombinant protein production is by optimisation of cell culture conditions to increase productivity, yield, titre and cell viability. Adjustments to cell culture conditions may have far-reaching effects on various aspects of the cell culture and, therefore, each adjustment needs to be studied carefully in order to ensure that its overall effect is beneficial to the production of the recombinant protein. Optimisation of the production of therapeutic proteins remains a challenge, since the effect of making multiple adjustments to cell culture conditions is unpredictable, particularly when the protein is produced at large scale.

As well as adjustments to the ingredients and components of the cell culture medium, such as vitamins, minerals, energy sources and the ratios thereof, the duration of the cell culture may also be manipulated, together with factors such as the pH and temperature of the cell culture. However, merely increasing the cell viability and/or the titre during protein production (i.e. increasing productivity) may have a detrimental effect on the quality of the recombinant protein. Attributes such as protein aggregates, fragments and glycosylation patterns, may all be affected by small changes in the culture conditions. Therefore, there remains a need in the pharmaceutical industry to increase cell viability and protein titre whilst at the same time maintaining protein quality.

SUMMARY OF THE INVENTION

The present invention provides a cell culture method for producing a TNFα binding protein, the method comprising maintaining the cell culture at a pH of about 6.50 to about 7.50 and at a temperature of about 31° C. to about 35° C. for at least 5 consecutive days of the duration of the cell culture, wherein cell viability is maintained at a level of at least 80% for up to 14 days in cell culture.

In an embodiment of the present invention, the cell culture method has a duration of up to 17 days. In an embodiment of the present invention, the cell viability is maintained at least 90%. In an embodiment of the present invention, the pH is maintained at about 6.75 to 7.20. In an embodiment of the present invention, the pH is maintained at about 6.80 to about 6.90. In an embodiment of the present invention, the pH is maintained at 6.88. In an embodiment of the present invention, the temperature is maintained at about 32° C. to about 34° C. In an embodiment of the present invention, the temperature is maintained at about 33° C. In an embodiment of the present invention, the cell culture is supplemented with a feed medium on one or more of day 3, 4, 5, 6, 7, 8, 9, 10, 11, 12, 13 or 14 of the cell culture method.

In an embodiment of the present invention, the feed medium comprises one or more of Cu, Zn and Se. In an embodiment of the present invention, the Cu is added to the cell culture to a concentration of between about 0.5 µM and about 1 µM, in addition to any Cu already present in the cell culture. In an embodiment of the present invention, the Zn is added to the cell culture at a concentration of between about 10 µM and about 80 µM, in addition to any Zn already present in the cell culture. In an embodiment of the present invention, the Se is added to the cell culture at a concentration of between about 30 nM and about 200 nM.

In an embodiment of the present invention, the cell culture comprises a culture of CHO cells. In an embodiment of the present invention, the cell culture comprises cell culture medium, wherein the cell culture medium is serum-free. In an embodiment of the present invention, the cell culture comprises cell culture medium, wherein the cell culture medium is protein-free.

In an embodiment of the present invention, the pH of the cell culture is maintained with $CO_2$ at a concentration of 20%. In an embodiment of the present invention, the temperature is maintained at 33° C. after being at 37° C. for at least one day of the cell culture method. In an embodiment of the present invention, the temperature is reduced to 33° C. after being at 37° C. for at least 4 consecutive days of the cell culture method. In an embodiment of the present invention, the pH is maintained at 6.8 after being at 7.5 for at least one day of the cell culture method. In an embodiment of the present invention, the pH is maintained at 6.8 after being at 7.5 for at least four consecutive days of the cell culture method.

In an embodiment of the present invention, the TNFα binding protein is an antibody. In an embodiment of the present invention, the antibody is adalimumab, infliximab or a biosimilar thereof. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine. In an embodiment of the present invention, the TNFα binding protein is etanercept or a biosimilar thereof.

The present invention also provides a recombinant protein obtainable by any of the above mentioned methods. In an embodiment of the present invention, the protein is a TNFα binding protein. In an embodiment of the present invention, the TNFα binding protein is an antibody. In an embodiment of the present invention, the antibody is adalimumab, infliximab, or a biosimilar thereof. In an embodiment of the present invention, the antibody is adalimumab or a biosimilar thereof having: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a pharmaceutical composition comprising any of the above mentioned recombinant proteins. In an embodiment of the present invention, the recombinant protein is an adalimumab biosimilar. In an embodiment of the present invention, wherein the recombinant protein is an antibody having: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a method of making a protein in a cell culture, comprising growing a host cell in a cell culture medium, expressing the protein in the host cell, maintaining the cell culture at a pH of about 6.50 to about 7.50 and at a temperature of about 31° C. to about 35° C. for at least 5 consecutive days of the duration of the cell culture, wherein cell viability is maintained at a level of at least 80% for up to 14 days in cell culture, and purifying the protein from the cell culture. In an embodiment of the present invention, the cell culture method has a duration of up to 17 days. In an embodiment of the present invention, the cell viability is maintained at least 90%. In an embodiment of the present invention, the pH is maintained at about 6.75 to 7.20. In an embodiment of the present invention, the pH is maintained at about 6.80 to about 6.90. In an embodiment of the present invention, the pH is maintained at 6.88. In an embodiment of the present invention, the temperature is maintained at about 32° C. to about 34° C. In an embodiment of the present invention, the temperature is maintained at about 33° C. In an embodiment of the present invention, the cell culture is supplemented with a feed medium on one or more of day 3, 4, 5, 6, 7, 8, 9, 10, 11, 12, 13 or 14 of the cell culture method.

In an embodiment of the present invention, the feed medium comprises one or more of Cu, Zn and Se. In an embodiment of the present invention, the Cu is added to the cell culture to a concentration of between about 0.5 µM and about 1 µM, in addition to any Cu already present in the cell culture. In an embodiment of the present invention, the Zn is added to the cell culture at a concentration of between about 10 µM and about 80 µM, in addition to any Zn already present in the cell culture. In an embodiment of the present invention, the method of claim 34, wherein the Se is added to the cell culture at a concentration of between about 30 nM and about 200 nM.

In an embodiment of the present invention, the cell culture comprises a culture of CHO cells. In an embodiment of the present invention, the cell culture comprises cell culture medium, wherein the cell culture medium is serum-free. In an embodiment of the present invention, the cell culture comprises cell culture medium, wherein the cell culture medium is protein-free.

In an embodiment of the present invention, the pH of the cell culture is maintained with $CO_2$ at a concentration of 20%. In an embodiment of the present invention, the temperature is maintained at 33° C. after being at 37° C. for at least one day of the cell culture method. In an embodiment of the present invention, the temperature is reduced to 33° C. after being at 37° C. for at least 4 consecutive days of the cell culture method. In an embodiment of the present invention, the pH is maintained at 6.8 after being at 7.5 for at least one day of the cell culture method. In an embodiment of the present invention, the pH is maintained at 6.8 after being at 7.5 for at least four consecutive days of the cell culture method.

In an embodiment of the present invention, the protein is a TNFα binding protein. In an embodiment of the present invention, the TNFα binding protein is an antibody. In an embodiment of the present invention, the antibody is adalimumab, infliximab or a biosimilar thereof. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a recombinant protein obtainable by any of the above methods of making. In an embodiment of the present invention, the recombinant protein is a TNFα binding protein. In an embodiment of the present invention, the TNFα binding protein is an antibody. In an embodiment of the present invention, the antibody is adalimumab, infliximab, or a biosimilar thereof. In an embodiment of the present invention, the antibody is adalimumab or a biosimilar thereof, wherein the antibody has: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides pharmaceutical compositions comprising any one of the above mentioned recombinant proteins. In an embodiment of the present invention, the recombinant protein is an adalimumab biosimilar. In an embodiment of the present invention, the recombinant protein is an antibody having: (i) a light chain sequence having at least 90% identity with SEQ ID NO: 1 and a heavy chain sequence having at least 90% identity with SEQ ID NO: 2; (ii) a light chain sequence having at least 95% identity with SEQ ID NO: 1 and a heavy chain sequence having at least 95% identity with SEQ ID NO: 2; (iii) a light chain sequence of SEQ ID NO: 1 and a heavy chain sequence of SEQ ID NO: 2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

BRIEF DESCRIPTION OF FIGURES

The invention is described below with reference to the following figures in which.

DETAILED DESCRIPTION

Figure 1:
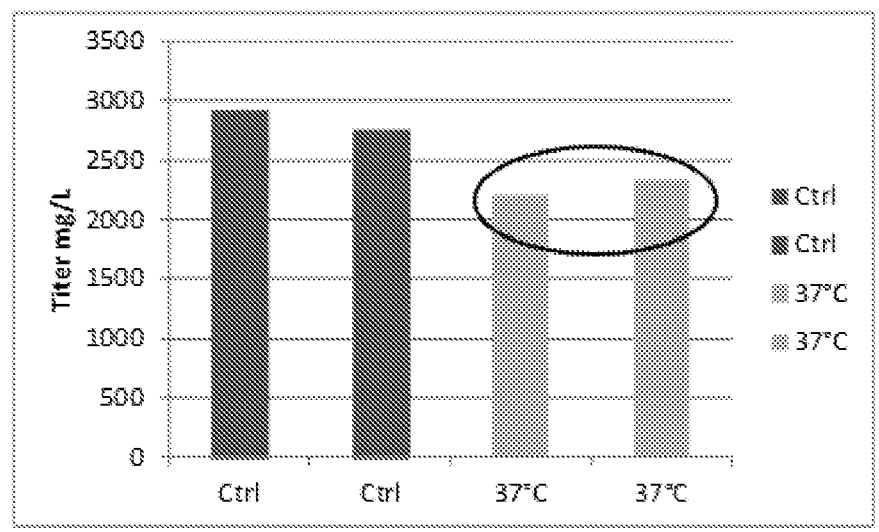
FIG. 1 shows the impact of cell culture temperature on protein titre.

The present invention relates to a method of maintaining cell viability of at least about 80% for up to 14 days in a cell culture producing a recombinant protein, the method comprising maintaining the cell culture at a pH of 6.5 to 7.5 and at a temperature of 31 to 35° C. for at least 5 consecutive days of the cell culture period. The cell viability is preferably maintained at least about 85%, or at least about 90% or at least about 95%. The pH may be maintained at a pH of 6.80 to 7.20, or at a pH of 6.80 to 6.90. The pH may be 6.88. In an embodiment of the present invention, the recombinant protein is a TNFα binding protein.

The present invention also provides a method of producing a protein comprising expressing the protein in a host cell growing in a cell culture medium, maintaining the cell culture at a pH of 6.5 to 7.5 and at a temperature of 31 to 35° C. for at least 5 consecutive days of the cell culture period, wherein cell viability of at least about 80% is maintained for up to 14 days in the cell culture, and purifying the protein from the cell culture. In embodiments of the present invention, the protein is a recombinant protein, a TNFα binding protein, an antibody, or a TNFα binding antibody.

In an embodiment of the present invention, the cell culture may be a fed-batch culture. In an embodiment of the present invention, the cell culture method may have a duration of up to 17 days.

In an embodiment of the present invention, the method of maintaining cell viability may include maintaining the temperature at about 32° C. to about 34° C., for at least 5 days. In an embodiment of the present invention, the temperature may be maintained at about 33° C. for at least 5 days. In an embodiment of the present invention, the cell culture medium may be supplemented with a feed medium on one or more of day 3, 4, 5, 6, 7, 8, 9, 10, 11, 12, 13 or 14.

In an embodiment of the present invention, the feed medium may comprise one or more of copper (Cu), zinc (Zn), or selenium (Se). The Cu may be added to the cell culture medium to a concentration of between about 150 nM and 750 nM in addition to any Cu already in the medium (if any). The Zn may be added to the cell culture medium to a concentration of between about 7 μM and about 25 μM, in additional to any Zn already present in the culture medium. The Se may be added to the cell culture medium to a concentration of about 10 nM and about 100 nM, in addition to any Se already present in the cell culture medium.

In the method of the invention, the culture of cells may be a culture of eukaryotic cells, more preferably a culture of mammalian cells, and most preferably a culture of Chinese hamster ovary (CHO) cells.

In order to maximise the production of a recombinant protein produced by cells in a cell culture, the effects of culture pH and temperature on cell growth, cell viability and optimum protein titre were investigated by the present inventors. The adjustment or manipulation of culture conditions can affect the outcome in terms of cell viability, protein quality, yield and titre.

This is particularly important when the recombinant protein produced is for therapeutic purposes since it is highly important to retain consistency in the structure and post-translational modifications of the particular protein, as well as maintenance of the cell culture productivity.

This can be illustrated by referring to the example of therapeutic antibodies and biosimilars thereto. A composition of recombinant proteins has a particular glycosylation pattern, as well as comprises a proportion of certain variants such as acidic or basic variants, (often known as a charge profile). The charge profile comprises a main peak, (which normally comprises around 70 to 80% of the antibody), a proportion of acidic variants (post translation modifications including amidation and/or disulphide reduction) and basic variants (include glycosylation variants). The post translation modifications may contribute to the pharmacokinetics and, thus, the therapeutic effects of the protein. Therefore, when producing biosimilars, it is necessary that the charge profile and glycosylation pattern of the biosimilar molecule is closely matched to the charge profile and glycosylation pattern as the reference protein.

It is of benefit to increase protein production (via increased titre, yield or cell viability) for commercial reasons. Problems may arise when attempting to maximise protein production, whilst maintaining the biosimilarity of the protein to the reference protein.

In an embodiment of the present invention, the cell culture temperature may be maintained at about 31° C. to about 35° C. and the pH may be maintained at about 6.8 to about pH 7.2 for at least 5 consecutive days during the cell culture duration, which was found to increase the titre of protein whilst at the same time maintaining an acceptable charge profile. In some embodiments of the present invention, the pH may be maintained at about 6.85, 6.90, 6.95, 7.00, 7.05, 7.10 or 7.15. In an embodiment of the present invention, the pH may be maintained for at least 5 days at a pH of between about 6.80 and about 7.20. In some embodiments, the pH may be maintained at this level for 5, 6, 7, 8, 9, 10, 11, 12, 13 or 14 consecutive days. In other embodiments, the pH may be maintained at between 6.8 and 6.9. In an embodiment of the present invention, the pH is maintained at 6.88. In some embodiments, prior to being maintained at pH 6.88 the pH of the culture may be maintained at 7.10 or less for 1, 2, 3, 4 or 5 consecutive days. In an embodiment of the present invention, the pH may be maintained at a value of less than or equal to 7.10 until day 5 of the cell culture method when it is reduced to 6.88.

The pH may be reduced by any method known in the art, such as with HCl, $CO_2$ or any other acidic medium. In an embodiment of the present invention, the pH may be reduced with carbon dioxide ($CO_2$). In another embodiment, the cell culture may be carried out in the presence of $CO_2$. In some embodiments of the present invention, the $CO_2$ may be at a concentration of about 12%, 15%, 20%, 22% or 25%. In an embodiment of the present invention, the $CO_2$ may beat a concentration of about 20%. In an embodiment of the present invention, the pH may be maintained for at least 5 days with $CO_2$ at 20%.

In embodiments of the present invention, the temperature of the cell culture may be maintained at a temperature of 31° C. to 35° C. for at least 4 consecutive days or 5 consecutive days. In some embodiments, the temperature be maintained at a temperature of 31° C., 32° C., 33° C., 34° C., 35° C. for at least 4 days or 5 days. In other embodiments, the temperature may be maintained at such a temperature for at least 6, 7, 8, 9, 10, 11, 12, 13 or 14 consecutive days. In embodiments of the present invention, the temperature may be maintained at about 33° C. for a specified period as defined above. In an embodiment of the present invention, the temperature is maintained at 33° C. from day 5 of the cell culture method until the end of the culture duration. In another embodiment of the present invention the temperature of the cell culture medium is maintained at 33° C. from days 5 to 14.

In embodiments of the present invention, the temperature of the cell culture on day 0 is between about 36° C. and about 37° C. In some embodiments, the temperature may be about 36.5°. In other embodiments, the temperature may be maintained at about 36° C., about 36.5° C. or about 37° C. for day 0, 1, 2, 3, 4 of the cell culture method and decreased to about 33° C. on day 5 of the culture method. In some embodiments, the temperature may be maintained at 33° C. following at least one day at 37° C., or following at least 2, 3 or 4 consecutive days at 37° C.

As mentioned above, many factors influence the cell viability, protein titre and protein quality. Therefore, the cell culture medium must be supplemented (for example, by way of a feed medium) in order to maintain sufficient nutrients in the cell culture to ensure the cells can continue growing, dividing and producing protein. Embodiments of the present invention also encompass maintaining cell viability at 80% for at least 14 days in a fed-batch cell culture, wherein the cell culture medium is supplemented on one or more of day 3, 4, 5, 6, 7, 8, 9, 10, 11, 12, 13 or 14. In some embodiments, the supplement may include one or more of essential amino acids, metal ions, minerals, vitamins and/or an energy source. In other embodiments, the supplement preferably comprises one or more of copper, zinc or selenium. In some embodiments, the supplement may be added to the cell culture medium on day 0, day 3, day 5, day 7, day 10 and/or day 14.

In embodiments of the present invention, the supplement addition to the cell culture medium may result in the concentration of copper added to the cell culture medium to be between about 100 nM and about 1000 nM, between about 125 nM and about 800 nM, or between 150 nM and about 725 nM, in addition to any copper already present in the culture medium. In some embodiments, the concentration of copper added to the cell culture medium by way of the addition of the feed medium may be about 159 nM, 314 nM, 353 nM, 380 nM, 547 nM or 706 nM, in addition to any copper already present in the cell culture medium.

In embodiments of the present invention, the addition of the feed medium to the cell culture medium may result in the concentration of zinc to be between about 3.0 µM and about 25.0 µM, in addition to any zinc already present in the cell culture medium, or between about 5.0 µM and about 22.0 µM, or between about 5.0 µM and about 20.0 µM. In some embodiments, the concentration of zinc added to the culture medium may be about 5.1 µM, 10.0 µM, 10.2 µM, 14.7 µM or 20.0 µM, in addition to any zinc already present in the cell culture medium.

In embodiments of the present invention, the addition of selenium to the cell culture medium by way of a feed medium may result in the concentration of selenium in the cell culture medium, after the addition of the feed medium, to be between about 10 nM and about 80 nM, in addition to any selenium already present in the cell culture media, or between about 13 nM and about 78 nM. In some embodiments, the selenium concentration in the cell culture medium after the addition of selenium may be about 13 nM, 25 nM, 33 nM, 38 nM, 50 nM or 76 nM, in addition to any selenium already present in the medium.

By maintenance of cell viability it is meant that cell viability is at a level of at least about 80% of alive (viable) cells, i.e. up to 20% of cells are dead (non-viable) of the total number of cells in the cell culture medium. In some embodiments, the cell viability may be at a level of at least about 82%, at least about 85%, at least about 90%, at least about 95% of total cells. Measurement of cell viability (i.e. number of alive cells as a % of the total) may be by any method known in the art, such as by a MTT cell viability assay.

Preferably, the cell culture medium is free of serum and/or free of protein and neither serum nor protein are added to the culture medium during the duration of the cell culture period. By free of protein it is meant free of protein supplements added or contained within the cell culture medium e.g. hydrolysates.

In an embodiment of the present invention, the cells may be eukaryotic cells, more preferably mammalian cells, and most preferably Chinese hamster ovary (CHO) cells.

In an embodiment of the present invention, the recombinant protein may be a TNFα binding protein. In some embodiments, the TNFα binding protein may be an antibody. In some embodiments, the TNFα binding protein may be a TNFα antibody, and wherein the TNFα antibody has (i) a light chain sequence of SEQ ID NO: 1 and a heavy chain sequence of SEQ ID NO: 2, or (ii) a light chain sequence having at least 90% identity with SEQ ID NO:1 and a heavy chain sequence having at least 90% identity with SEQ ID NO:2, or (iii) a light chain sequence having at least 95% identity with SEQ ID NO:1 and a heavy chain sequence having at least 95% identity with SEQ ID NO:2, particularly including adalimumab or a biosimilar thereof. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine. As used herein, "adalimumab" refers to any human monoclonal antibody that specifically binds a tumour-necrosis factor (TNF)-α, having the light chain sequence of SEQ ID NO: 1 and the heavy chain sequence of SEQ ID NO: 2. Adalimumab is sold under the trade name Humira® and has CAS designation 33-1731-18-1. In an embodiment of the present invention, the TNFα binding protein may be a TNFα antibody, wherein the antibody is infliximab or a biosimilar thereof. As used herein, "infliximab" refers to any chimeric monoclonal antibody that specifically binds to TNFα, is sold under the trade names Remicade®, Remsima®, and/or Inflectra®, and has CAS designation number 170277-31-3. In an embodiment of the present invention, the TNFα binding protein may be etanercept. As used herein, "etanercept" refers to any fusion protein that inhibits a TNFα, is sold under the trade name Enbrel®, and has Chemical Abstracts Service (CAS) designation number 185243-69-0.

As used herein, the term "about" or "approximately" has its general meaning as understood to one of skill in the art within the context of the referenced value or range. In some embodiments, as understood to one of skill in the art, the term "about" or "approximately" means within 20%, 15%, 10%, 9%, 8%, 7%, 6%, 5%, 4%, 3%, 2%, 1%, 0.5%, or 0.05% of a given value or range.

The term "amino acid" as used herein refers to any of the twenty naturally occurring amino acids that are normally used in the formation of polypeptides, or analogs or derivatives of those amino acids as understood by the skilled person. Amino acids may be provided in the cell culture medium to the cell culture. The amino acids provided in the medium may be provided as salts or in hydrate form.

The term "antibody" is used as understood in the art, i.e. an immunoglobulin molecule that recognises and specifically binds to a target, such as a protein, polypeptide, peptide, carbohydrate, polynucleotide, lipid, or combinations of the foregoing etc., through at least one antigen recognition site within the variable region of the immunoglobulin molecule. The term encompasses, as understood in the art, intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of IgA, IgD, IgE, IgG, and IgM, and include, for example IgG1, IgG2, IgG3, IgG4, IgA1 and IgA2.

The term "basal cell culture medium" as used herein refers to any cell culture medium used to culture cells that has not been modified either by supplementation, or by selective removal of a certain component.

The term "batch culture" as used herein refers to a method of culturing cells in which all the components that will ultimately be used in culturing the cells, including the medium as well as the cells themselves, are provided at the beginning of the culturing process i.e. day 0. A batch culture is typically stopped at some point and the cells and/or components in the medium are harvested and optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 litre and may be 10, 100, 250, 500, 1000, 2500, 5000, 8000, 10,000, 12,000, 15,000 litres or more, or any volume in between. The internal conditions of the bioreactor are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 litres and may be 1000, 2000, 2500, 5000, 8000, 10,000, 12,0000 litres or more, or any volume in between. One of ordinary skill in the art will be aware of and will be able to choose suitable bioreactors for use in practicing the present invention.

As used herein, "biosimilar" (of an approved reference product/biological drug, such as a protein therapeutic, antibody, etc.) refers to a biologic product that is highly similar to a reference product notwithstanding minor differences in clinically inactive components having no clinically meaningful differences between the biological product and the reference product in terms of the safety, purity, and potency of the product. In one embodiment, the biosimilar biological product is biosimilar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

The term "cell density" as used herein refers to that number of cells present in a given volume of medium.

The terms "culture" and "cell culture" as used herein refer to a eukaryotic cell population that is suspended in a cell culture medium under conditions suitable to survival and/or growth of the cell population. As will be clear to those of ordinary skill in the art, these terms as used herein may refer to the combination comprising the mammalian cell population and the cell culture medium in which the population is suspended.

The term "fed-batch culture" as used herein refers to a method of culturing cells in which additional components are provided to the culture at some time subsequent to the beginning of the culture process i.e. after day 0. The provided components typically comprise nutritional supplements for the cells which have been depleted during the culturing process. A fed-batch culture is typically stopped at some point and the cells and/or components in the medium are harvested and optionally purified.

As used herein, "growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. For a particular cell line, the period of time and conditions are determined to be optimal for cell growth and division. During the growth phase, cells are cultured in nutrient medium containing the necessary additives, in a controlled atmosphere, such that optimal growth is achieved for the particular cell line. Cells are maintained in the growth phase for a period of about between one and four days, usually between two to three days.

As used herein, "production phase" of the cell culture refers to the period of time during which cell growth has plateaued. During the production phase, logarithmic cell growth has ended and protein production is primary. During this period of time the medium is generally supplemented to maintain cell viability.

The term "expression" or "expresses" are used herein to refer to transcription and translation occurring within a host cell. Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The terms "medium", "cell culture medium" and "culture medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined medium" such as a serum-free medium and/or protein free medium that contains no proteins, hydrolysates or components of unknown composition. Defined media are free of animal-derived components and all components have a known chemical structure.

The terms "protein" as used herein refers to a sequential chain of amino acids linked together via peptide bonds, also referred to interchangeably with the term "polypeptide". The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does not require permanent physical association with other polypeptides in order to form the discrete functioning unit, the term "protein" as used herein refers to the single polypeptide. If discrete functional unit is comprised of more than one polypeptide that physically associate with one another, the term "protein" as used herein refers to the multiple polypeptides that are physically coupled and function together as the discrete unit, such as an antibody.

"Recombinantly expressed polypeptide" and "recombinant polypeptide or protein" as used herein refer to a polypeptide expressed from a mammalian host cell that has been genetically engineered to express that polypeptide. The recombinantly expressed polypeptide can be identical or similar to polypeptides that are normally expressed in the mammalian host cell. The recombinantly expressed polypeptide can also be foreign to the host cell (i.e. exogenous). Alternatively, the recombinantly expressed polypeptide can be chimeric in that portions of the polypeptide contain amino acid sequences that are identical or similar to polypeptides normally expressed in the mammalian host cell, while other portions are foreign to the host cell.

The term "titre" as used herein refers to the total amount of recombinantly expressed polypeptide or protein produced by a mammalian cell culture divided by a given amount of medium volume. Titre is typically expressed in units of milligrams of polypeptide or protein per milliliter of medium. Protein titre can be measured by any method known in the art, such as by BioCore assay.

By "to a concentration of" it is meant in additional to any of that metal ion already present in the cell culture medium. It is assumed that the cell culture has been depleted of the particular metal ion. However, there may be some residual amounts remaining, and the concentration to which the metal ion or amino acid is added does not take into account any residual amount.

As used herein, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Those of ordinary skill in the art will understand that various modifications to these preferred embodiments are within the scope of the appended claims. It is the claims and equivalents thereof that define the scope of the present invention, which is not and should not be limited to or limited by this description of certain preferred embodiments.

The present invention provides a method for the production of proteins by cell culture. In particular, the invention provides a method maintaining cell viability at a high level through the manipulation of pH and temperature conditions at certain points in the cell culture process. The importance of maintaining cell viability throughout the culture duration is clearly high, since the final titre of recombinant protein will be directly affected as the cell viability reduces.

Any polypeptide or protein that is expressible in a host cell may be produced in accordance with the method of the present invention. The polypeptide is preferably expressed from a gene that is introduced into the host cell through genetic engineering, i.e. a recombinant polypeptide. The polypeptide may be one that occurs in nature, or may alternatively have a sequence that was engineered or selected or altered by the hand of man. An engineered polypeptide may be assembled from other polypeptide segments that individually occur in nature, or may include one or more segments that are not naturally occurring.

Of particular relevance to the present invention is the production of antibodies and other binding proteins. Any antibody that can be expressed in a host cell may be used in accordance with the present invention. In one embodiment, the antibody to be expressed is a monoclonal antibody, and is preferably an antibody that specifically binds to TNFα, such as adalimumab or infliximab.

Particular antibodies can be made, for example, by preparing and expressing synthetic genes that encode the recited amino acid sequences or by mutating human germline genes to provide a gene that encodes the recited amino acid sequences. Moreover, these antibodies can be produced by any method known to one of skill in the art.

In one embodiment, the methods of the invention are used to produce an antibody that specifically binds a tumour-necrosis factor (TNF)-α. The antibody may be adalimumab or infliximab, or biosoimilars thereof. In an embodiment of the present invention, the TNFα antibody has (i) a light chain sequence of SEQ ID NO: 1 and a heavy chain sequence of SEQ ID NO: 2, or (ii) a light chain sequence having at least 90% identity with SEQ ID NO:1 and a heavy chain sequence having at least 90% identity with SEQ ID NO:2, or (iii) a light chain sequence having at least 95% identity with SEQ ID NO:1 and a heavy chain sequence having at least 95% identity with SEQ ID NO:2, particularly including adalimumab or a biosimilar thereof. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa is any naturally occurring amino acid; and has a heavy chain sequence comprising SEQ ID NO: 4, wherein Xaa is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

In embodiments of the present invention, the antibody is an antigen-binding fragment of a full length antibody, e.g., a Fab, F(ab')2, Fv or a single chain Fv fragment. In some embodiments, the antibody is a full length antibody. In some embodiments, the antibody can be a monoclonal antibody or a mono-specific antibody. In embodiments, the antibody can be a human, humanized, CDR-grafted, chimeric, mutated, affinity matured, deimmunized, synthetic or otherwise in vitro-generated antibody, and combinations thereof.

Any mammalian cell or cell type susceptible to cell culture, and to expression of polypeptides, may be utilized in accordance with the present invention as known in the art. In embodiments of the present invention, The methods may be applied in the culturing of and expression of polypeptides from CHO cell lines. In some embodiments, the cell line may be CHO—S.

The mammalian cell culture of the method of the present invention may be prepared in any medium suitable for the particular cell being cultured. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions, as well as any media that are well known to the person skilled in the art. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and glucose or an equivalent energy source. Any other necessary supplements may also be included at appropriate concentrations that would be known to those skilled in the art.

Additional amino acids and nutrients may also be used in accordance with standard cell culture techniques as known to the skilled person, for example to replenish essential amino acids as the cells multiply, replenish an energy source and replenish other essential micronutrients, such as trace elements.

The amount of supplementation required can vary depending on the cellular growth conditions. For example, factors that influence cellular consumption rates, will affect the amount of supplementation that is required to maintain cell viability, protein titre and protein quality attributes. Such factors include, but are not limited to, temperature, osmolality, and pH, as known in the art. As such, the present invention is concerned with the adjustment of pH and temperature throughout the cell culture duration to maximise cell viability, titre and protein quality. Embodiments of the present invention may also include the supplementation of the culture with one or more of copper, zinc or selenium.

The basal cell culture medium i.e. the medium in which the cell culture is started, prior to any additional supplementation may contain essential amino acids, vitamins (such as folic acid, biotin, thiamine), salts (such as sodium chloride, sodium bicarbonate), metal ions (such as, in the form of cupric sulphate, zinc sulphate or sodium selenite) all foaming agents (such as Pluronic©) and an energy source (such as glucose or galactose). The particular combination and amounts of each component may vary depending on the cell line, and the recombinant protein to be produced.

Various methods of preparing mammalian cells for production of proteins or polypeptides by fed-batch culture are well known in the art. Generally, the cells are first propagated or expanded in a step-wise procedure until a cell density is reached that is suitable for inoculating the bioreactor in which the method of the invention is to take place. Such methods of propagation or expansion can be carried out by any of the variety of methods well-known to one of ordinary skill in the art.

In accordance with the present invention, the culture size can be any volume that is appropriate for production of polypeptides. In one embodiment, the volume of the production bioreactor is at least 500 litres. In other embodiments, the volume of the production bioreactor is 1000, 2000, 2500, 5000, 8000, 10,000, 12,000 or 15,000 litres or more, or any volume in between. One of ordinary skill in the art will be aware of and will be able to choose a suitable culture size for use in practicing the present invention.

The cells may be allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. Embodiments of the present invention may involve maintaining the cell culture over a period of up to 14 or 17 days.

In accordance with the present invention, the cells may be maintained in the production phase (after the log phase) of the cell culture method until a desired cell density or production titre is reached. In one embodiment, the cells are maintained in the subsequent production phase until the titre to the recombinant polypeptide or protein reaches a maximum. In other embodiments, the culture may be harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. The cells may be allowed to grow for a defined period of time during the subsequent production phase.

An increased concentration of the amino acids may be added in the basal media prior to the cell culture process (i.e. at day 0) or else supplemented in the feed media in the fed-batch system, on any one or more of day 1, 2, 3, 4, 5, 6, 7, 8, 9, 10, 11, 12, 13 or 14.

In certain cases, it may be necessary to supplement the cell culture during the growth and/or subsequent production phase with nutrients or other medium components that have been depleted or metabolized by the cells. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, may all be added to the cell culture at one time, or they may be provided to the cell culture in a series of additions. In one embodiment of the present invention, the supplementary components are provided to the cell culture at multiple times in proportional amounts. In another embodiment, it may be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture may be 1, 2, 3, 4, 5, 6, 7, 8, 9, 10, 15, 20, 25, 30, 35, 40, 45 or 50% of the volume of the cell culture prior to providing the supplementary components.

As shown in the appended examples and figures, cell cultures of various sizes were tested in order to determine the optimum temperature and pH values and timings of any changes during the cell culture medium. As is shown, the adjustments made are transferable to any size of culture i.e. the culture method of the invention is able to be smoothly and successfully scaled up to a process suitable for producing commercial amount of the recombinant protein of the invention.

Individually, the alteration of the pH of a culture medium is known to enable manipulation of the ultimate protein product. Likewise, temperature of culture conditions has been shown to have subsequent effects when altered during the cell culture period.

However, the present inventors have established that the combination of a particular change in pH and a particular change in temperature, as well as the timings of such changes are important in obtaining predictable cell viability and thus, a high titre of recombinant protein. The particular changes and timings are not predictable. In particular, it is known in the art that the combined adjustment of two or more parameters that have been shown to have a positive effect on cell culture production or on the resultant protein qualities when applied individually, may result in a negative effect when applied in combination. Thus, the advantages of the combined temperature and pH changes of the method of the invention were unexpected.

As well as the effects of the temperature and pH shifts in the method of the invention, the addition of trace elements (including copper, selenium, zinc) as a feed medium rather than in the basal cell culture medium were found to be beneficial to cell viability and to protein titre. Again, as shown in the examples, the effects of the individual elements cannot not necessarily lead to the prediction of the effect of the use of all three elements in the cell culture medium, when combined with the pH and temperature parameters of the method of the invention In general, it will typically be desirable to isolate and/or purify proteins or polypeptides expressed according to the present invention. In one aspect, the expressed recombinant polypeptide or protein is secreted into the medium and thus cells and other solids may be removed, as by centrifugation or filtering for example, as a first step in the purification process. Further purification may be carried out by any method known to the skilled person.

Once purified, the protein or polypeptide (for example an antibody such as an anti-TNFα antibody described herein) can be formulated as a pharmaceutical composition for administration to a subject, e.g., to treat a disorder, such as an autoimmune disorder or disease.

The foregoing description is to be understood as being representative only and is not intended to be limiting. Alternative methods and materials for implementing the invention and also additional applications will be apparent to one of skill in the art, and are intended to be included within the accompanying claims.

EXAMPLES

Example 1

Impact of Temperature

Tests were performed in production medium with a feed medium added on day 3, 5, 7 and 10. The impact of a temperature of 37° C. during the whole culture was compared to the control where the temperature was shifted from 37° C. to 33° C. on day 5.

Titres are shown in FIG. 1. Titres were lower when the temperature was kept at 37° C. during the whole culture.

Example 2

Impact of pH ($CO_2$ 20%)

Tests were performed in production medium with a feed medium added on days 3, 5, 7 and 10. In order to induce a pH drop which might improve the titre of the molecule, previous test performed with $CO_2$ at 10% was repeated under improved conditions: samples were transferred to an incubator at 20% $CO_2$ on day 4.

A pH drop to 6.65 on day 5 was observed at CO2 20%, and pH was maintained between 6.65 and 6.92 from day 5 to day 14, while in the control, pH was maintained between 6.84 and 7.14.

Figure 2:
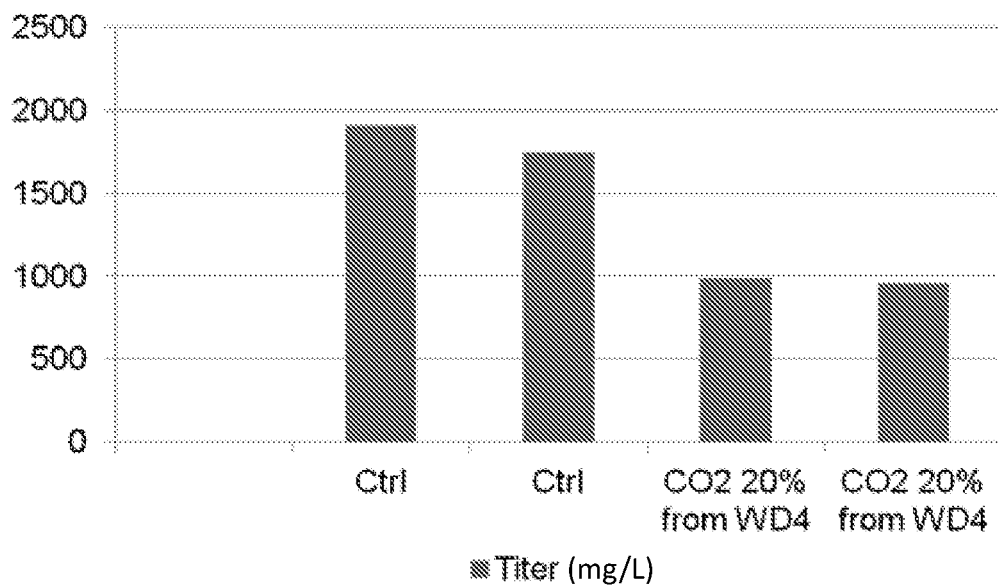
FIG. 2 shows the impact of $CO_2$ (20%) on protein titre.

Titres are shown in FIG. 2. A considerable decrease was observed with a lower pH. However, experiments combining pH and temperature shift were conducted in order to try to rectify this.

Example 3

Timing of Temperature Shift

Figure 3:
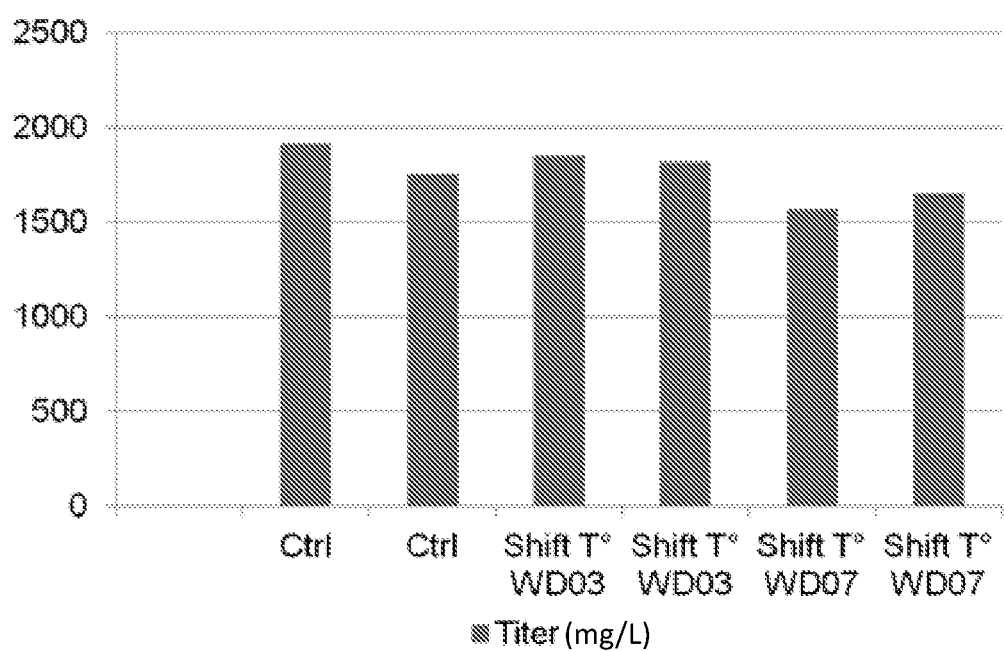
FIG. 3 shows the effect of a shift in temperature on protein titre.

The control with a temperature shift from 37° C. to 35° C. on day 5 (as determined in Example 1) was compared with a shift of temperature on day 3 and with a temperature shift on day 7. Titres on day 12 are shown in FIG. 3. Titres were slightly lower when the temperature shift was done on day 7.

Example 4 pH was further evaluated in a micro-scale bioreactor with internal probe control, with the following condition included in the improved process:

Low T° C. shift: 33° C. on day 5.

Conditions tested in this experiment are listed in Table 1.

Experimental Conditions

TABLE 1

| | Experimental conditions |
|---|---|
| 1 | Control (historical process) pH 7.1 with $CO_2$ |
| 2 | Shift pH 6.9 on day 4 maintained with $CO_2$ |
| 3 | Shift pH 6.8 on day 4 maintained with $CO_2$ |
| 4 | Shift pH 6.7 on day 4 maintained with $CO_2$ |
| 5 | Shift pH 6.7 on day 5 maintained with $CO_2$ |
| 6 | Shift pH 6.7 on day 7 maintained with $CO_2$ |
| 7 | Shift pH 6.8 on day 4 maintained with HCl |

TABLE 1-continued

| | Experimental conditions |
|---|---|
| 8 | Shift pH 6.8 on day 4 maintained with acetic acid |
| 9 | Shift pH 6.8 on day 4 maintained with lactic acid |

Process Performance

Figure 4A:
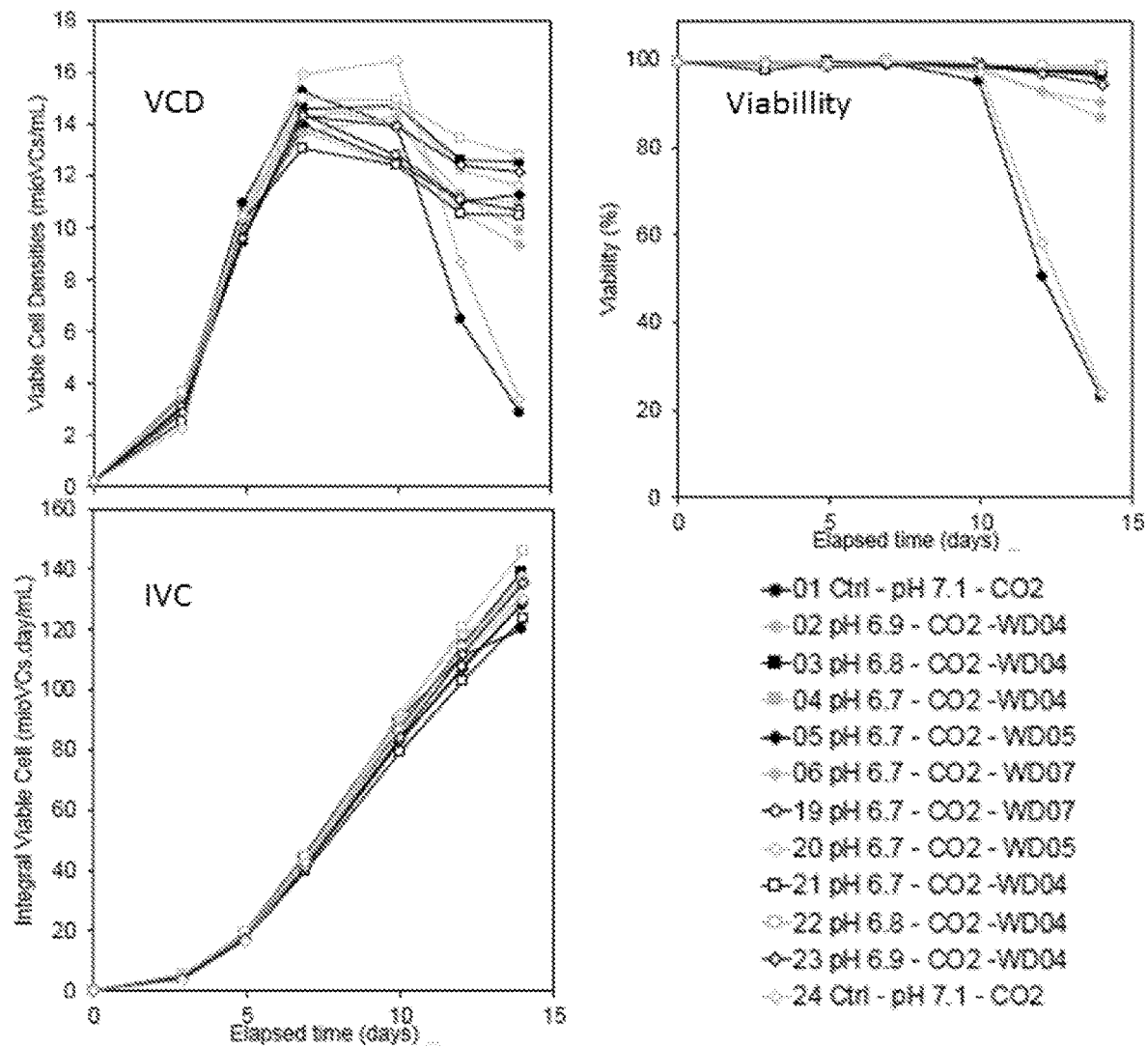
FIG. 4 A, B shows the results of models for the culture duration, temperature shift and pH shift on cell viability and titre.
Figure 4B:
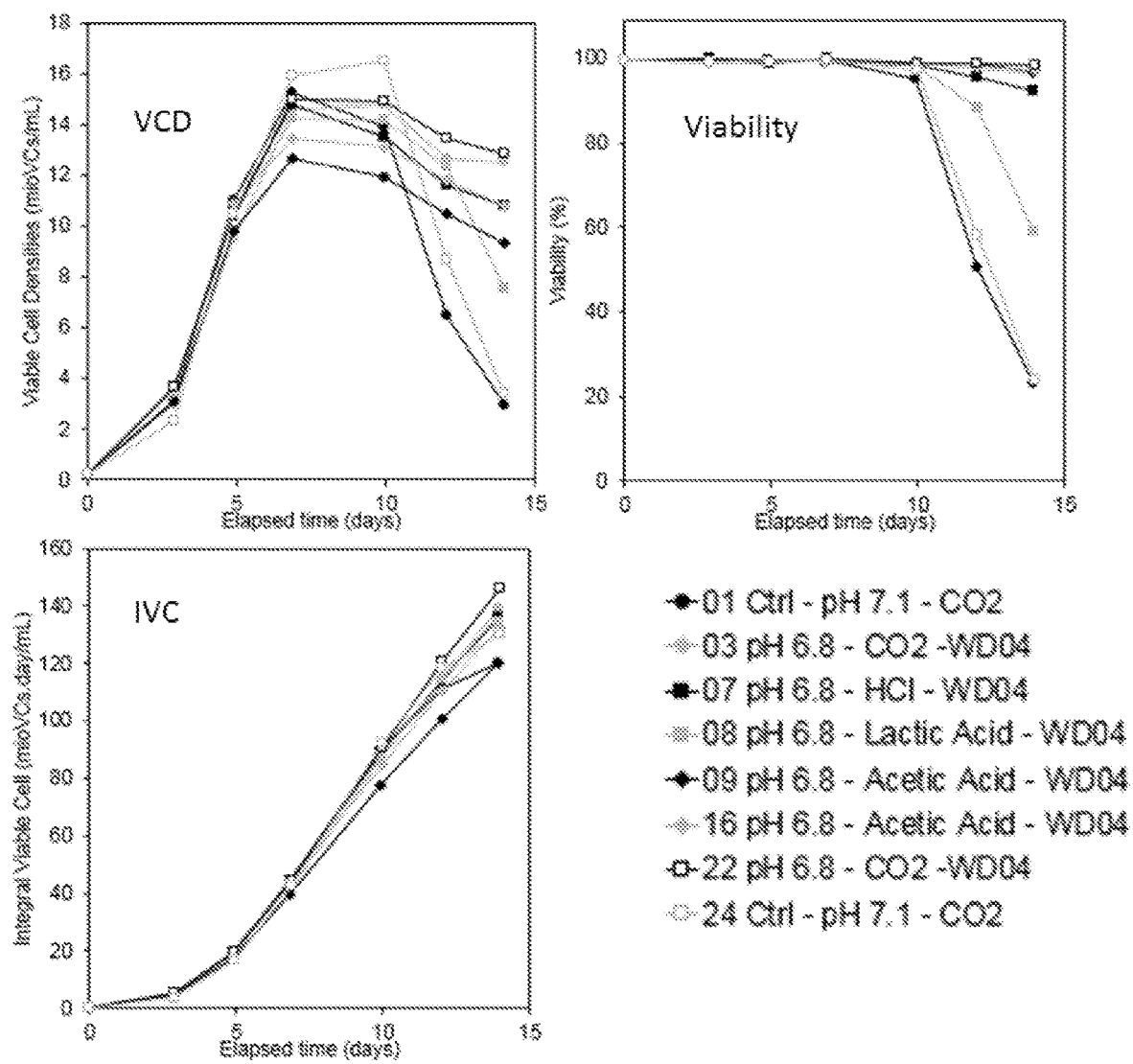

Cell Viability is Shown in FIGS. 4A and 4B.

Figure 5A:
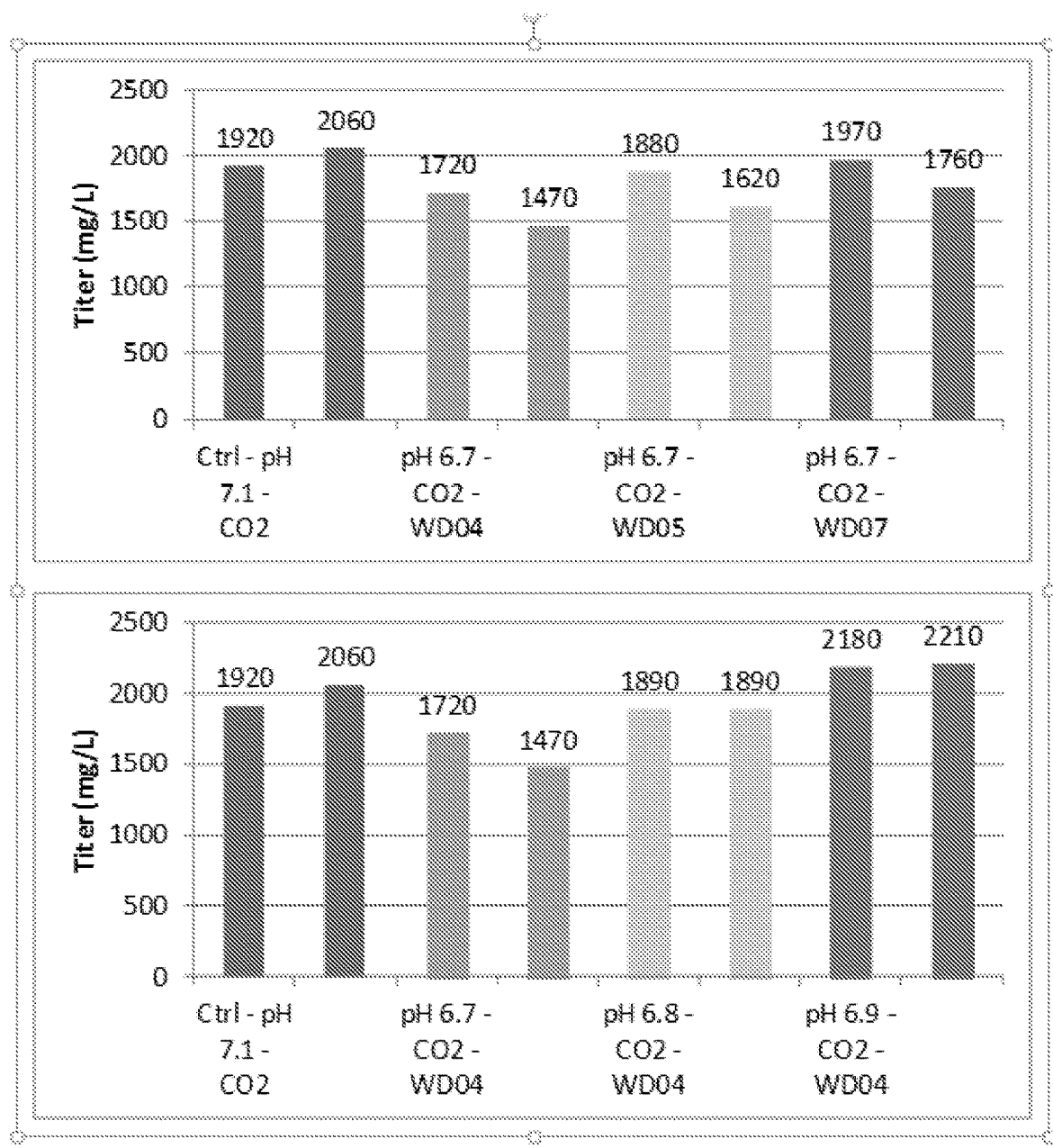
FIG. 5 A, B shows the effect of pH value, timings and control on cell viability.
Figure 5B:
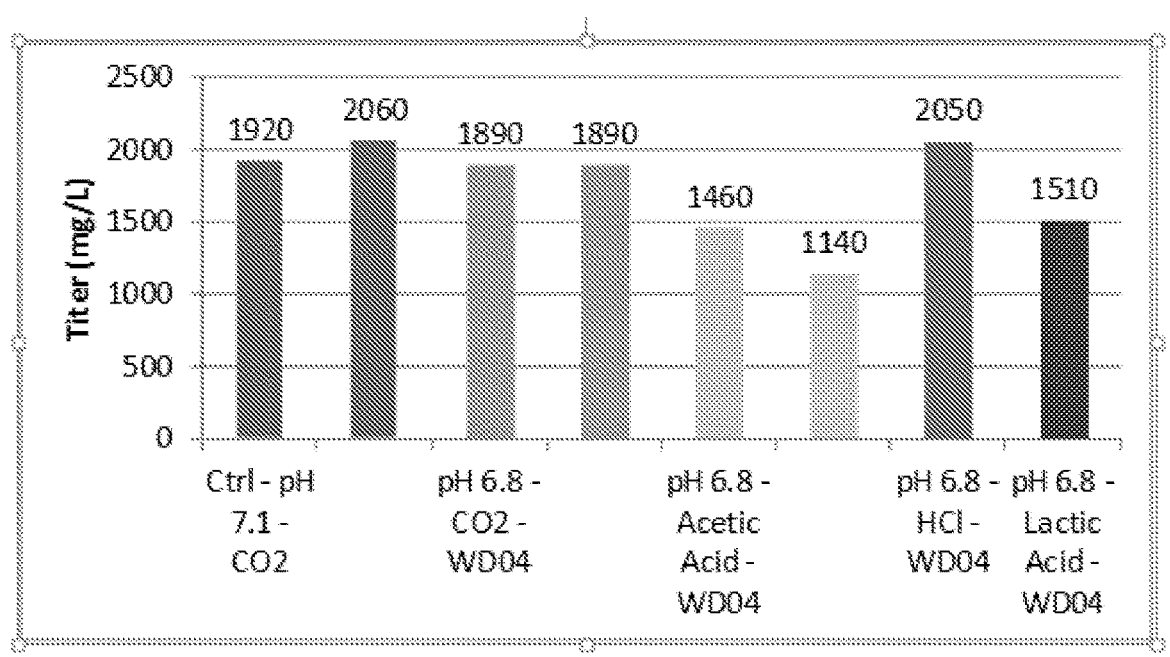

Globally, a pH shift to lower values enabled to maintain a good cell viability up to day 14, while in the control, the viability started to drop from day 8 (FIGS. 4A and 4B). With a pH shift to 6.8 on day 4, best final viability was obtained when pH regulation was performed with CO2 and with acetic acid (maximum viable cell density was slightly lower with acid acetic regulation). Results are also shown in FIGS. 5A and 5B.

Example 6

DoE Confirmation in 3.5 L Bioreactors

Following data obtained in OFAT studies, DoE studies and micro-scale bioreactors, confirmation runs were performed at 3.5 L scale with the following conditions included in the improved process:

Trace elements reduced in medium and main feed
Low T° C. shift: 33° C. on day 5
Low pH shift: 6.75 on day 5
Reduced amount of amino acid content in the feed Two different versions of this improved process were tested in 3.5 L bioreactors vs historical process. Experimental conditions tested were:

Low pH maintained with $CO_2$ in sparge
Low pH maintained with lactic acid 2.5M
  Despite a lower viability shown in micro-scale bioreactors, the evaluation of a lactic acid solution was kept for its reduction of pCO2 which might affect product quality.

Process Performance

Figure 6:
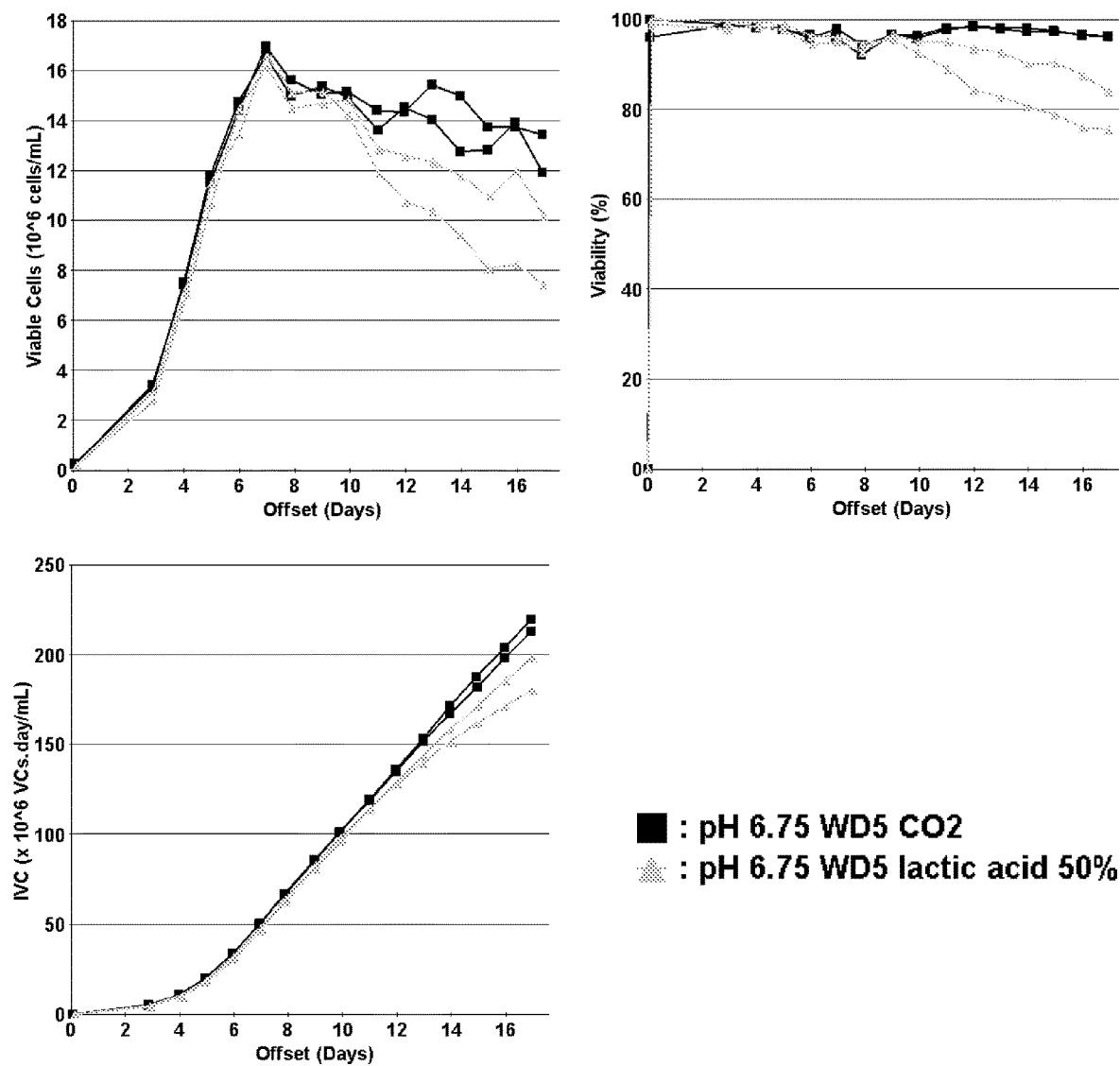
FIG. 6 shows the impact of pH value, timings and control on cell viability.

Viable cell density, cell viability and IVCs are shown in FIG. 6.

Cell growth and viability were similar for the improved process and the historical process, when the low pH was maintained with CO2. Cell viability was lower from day 10, when low pH was maintained by lactic acid.

Example 7

Repeatability Runs in 3.5 L Bioreactors.

A process was selected. Compared to the historical process, certain changes, including the following, were implemented:

T° C. shift: 33° C. on day 5
Low pH shift: 6.75 on day 5 by CO2 sparge
Process limited to 11 days Six runs were performed in parallel to test the reproducibility of this process. These runs were performed as 3 independent duplicates, with cells coming from 3 different cell expansions and seed trains, and using 3 different media and feed preparations.

Process Performance

Figure 7A:
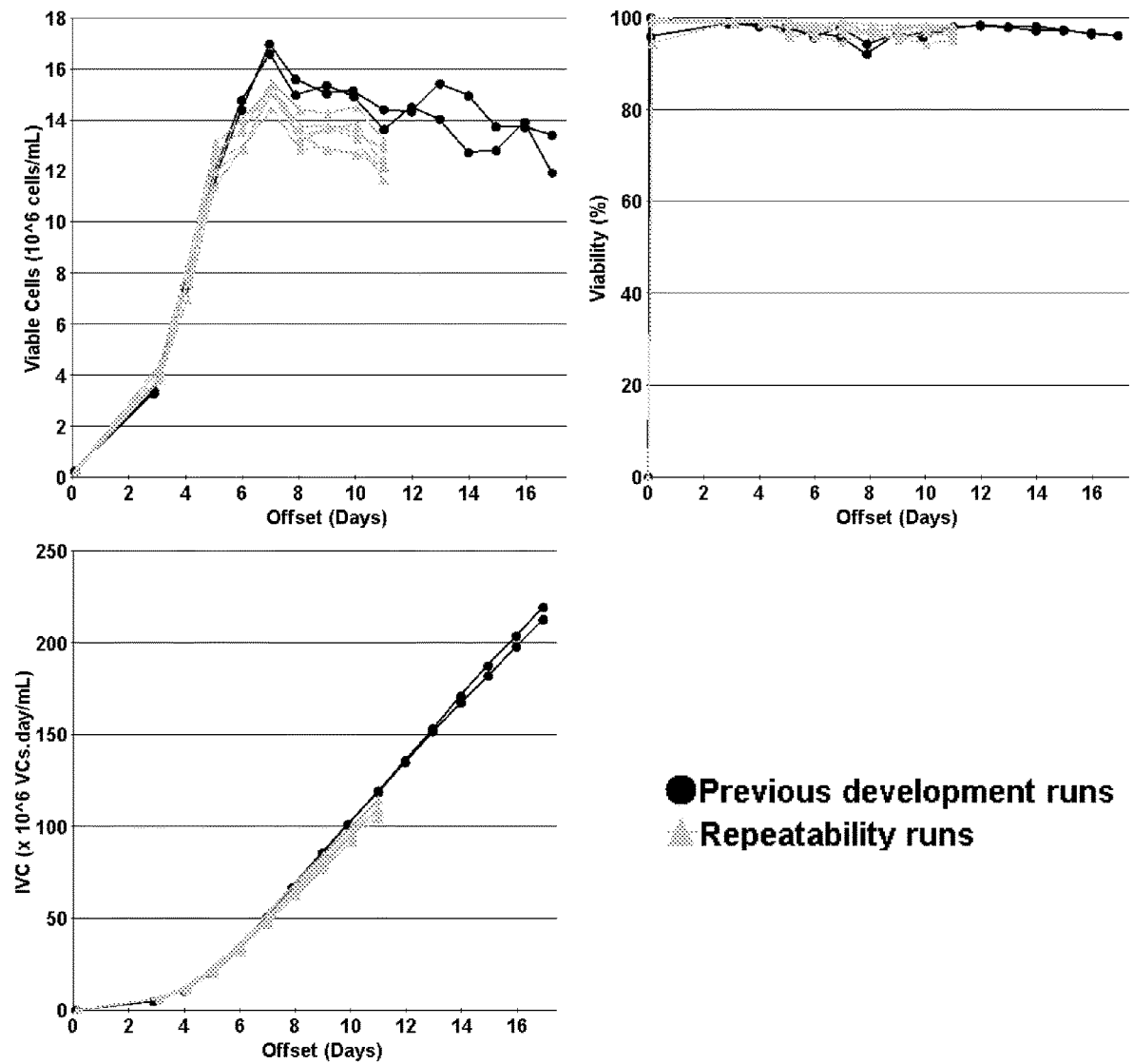
FIG. 7 A, B shows the effect of pH control on cell viability.
Figure 7B:
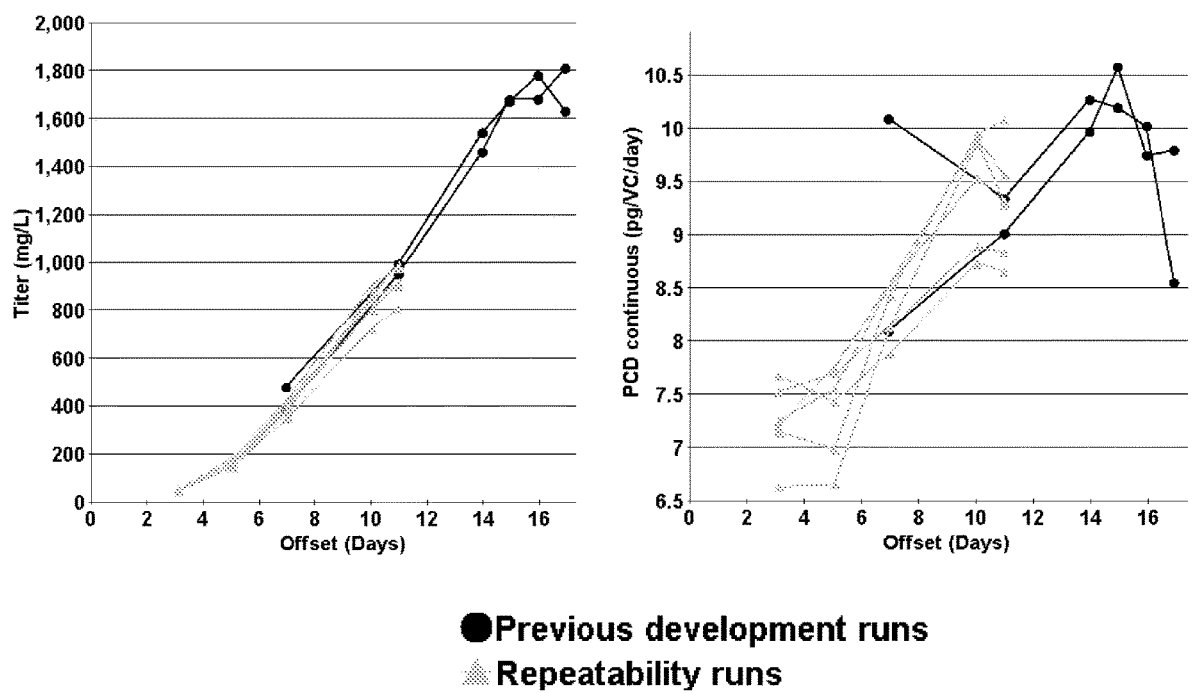

Repeatability runs were compared to previous development runs, performed under similar conditions. Viable cell density, cell viability and IVC are shown in FIG. 7A and titres and specific productivity in FIG. 7B.

Process performance, pH, pCO$_2$ profiles of repeatability runs were similar to previous development runs.

Example 8

Process in 280 L Bioreactors

A run at 280 L scale was performed in the same conditions as 3.5 L reproducibility runs.

Process Performance

Figure 8:
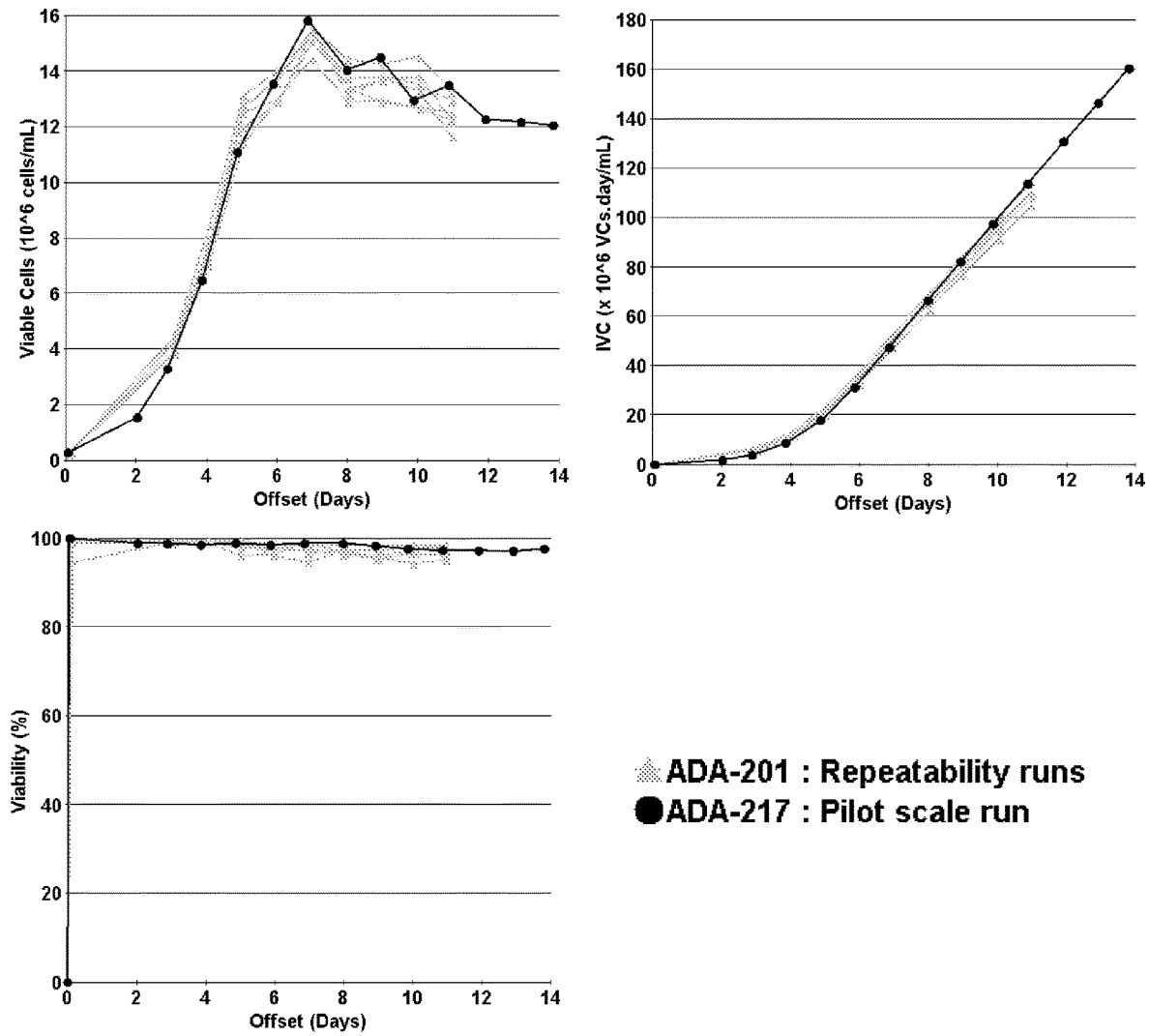
FIG. 8 shows the repeatability of the pH control on cell and titre.

Process performance and pCO$_2$, pH in 280 L bioreactors compared to repeatability runs in 3.5 L bioreactors are shown in FIG. 8. Viable cell densities, cell viabilities and IVCs in 280 L bioreactors were completely aligned with 3.5 L bioreactors.

CONCLUSION

During development studies, OFAT and DoE studies were performed in shake tubes and data confirmation was performed in bioreactors:

OFAT studies: various parameters including low pH (CO$_2$ 20%), temperature shift timing, culture duration and antifoam addition were tested in ST. These studies enabled to choose process parameters to be tested in a DoE.

DoE studies: A response surface with 3 centre points was designed for the study of the following parameters: low pH, temperature shift timings and culture duration. The culture duration, temperature, CO$_2$ were confirmed as important process parameters.

Experiment in micro-scale bioreactors: in parallel to DoE studies, pH was further evaluated in micro-scale bioreactors. A shift to a lower pH increased final cell viability, but tended to impair titres. It also had a positive impact on isoform profile. The best pH regulation was obtained with CO$_2$, compared to HCl, acetic acid and lactic acid.

DoE confirmation in 3.5 L bioreactors: following data obtained in OFAT studies, in DoE studies and confirmation runs were performed at 3.5 L scale with the following improved process:

Low temperature shift: 33° C. on day 5

Low pH shift: 6.75 on day 5

Different versions of this improved process were tested: low pH maintained with CO$_2$ in sparge or with lactic acid. Best results were obtained with the process with a low pH maintained with C02 in sparge. When reducing the culture duration to 11 days, no drop off in viability or titre was observed, indicating that a culture duration of at least 14 days is achievable.

Repeatability in 3.5 L bioreactors: 6 runs were performed in parallel to test the reproducibility of the improved process defined with the standard approach These runs were performed as 3 independent duplicates with cells coming from 3 different cell expansions and seed trains, and using 3 different media and feed preparations. Process performance and pH, pCO2 of repeatability runs were similar to previous development runs.

Process in 280 L bioreactor compared to 3.5 L repeatability runs: viable cell density, cell viability, and IVC were similar for the two scales. External pH was slightly higher at 280 L scale from day 6 (as it was the case for pCO2) although internal pH regulation was similar between scales. Titres and specific productivity were acceptable.

---

The invention claimed is:

1. A method of making a protein in a cell culture, comprising
   (i) growing a host cell in a cell culture medium,
   (ii) expressing the protein in the host cell,
   (iii) maintaining the cell culture at a pH of 7.1 to 7.5 and at a temperature of between about 36° C. and about 37° C. for at least 4 consecutive days of the cell culture method,
   (iv) reducing the temperature to about 33° C. and reducing the pH to 6.5 to 6.9 by addition of $CO_2$,
   (v) maintaining the concentration of $CO_2$ at about 20%, wherein cell viability is maintained at a level of at least 80% for up to 14 days in cell culture, and
   (vi) purifying the protein from the cell culture.

2. The method of claim 1, wherein the cell culture method has a duration of up to 17 days.

3. The method of claim 1, wherein the cell viability is maintained at least 90%.

4. The method according to claim 1, wherein the pH in step (iv) is reduced to about 6.8.

5. The method of claim 1, wherein the cell culture is supplemented with a feed medium on one or more of day 3, 4, 5, 6, 7, 8, 9, 10, 11, 12, 13 or 14 of the cell culture method.

6. The method of claim 5, wherein the feed medium comprises one or more of Cu, Zn and Se.

7. The method of claim 6, wherein the Cu is added to the cell culture to a concentration of between about 0.5 μM and about 1 μM, in addition to any Cu already present in the cell culture.

8. The method of claim 6 wherein the Zn is added to the cell culture at a concentration of between about 10 μM and about 80 μM, in addition to any Zn already present in the cell culture.

9. The method of claim 6, wherein the Se is added to the cell culture at a concentration of between about 30 nM and about 200 nM.

10. The method of claim 1, wherein the cell culture comprises a culture of CHO cells.

11. The method according to claim 1, wherein the cell culture comprises cell culture medium, wherein the cell culture medium is serum-free or protein-free.

12. The method according to claim 1, wherein the pH is maintained at 6.8 after being at 7.5 for at least four consecutive days of the cell culture method.

13. The method according to claim 1, wherein the protein is
   a. a TNFa binding protein; or
   b. an anti-TNFa antibody; or
   c. adalimumab, infliximab, or a biosimilar of adalimumab or a biosimilar of infliximab; or
   d. adalimumab or a biosimilar thereof having
      i. a light chain sequence of SEQ ID NO: 1 and a heavy chain sequence of SEQ ID NO: 2;
      ii. a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8;
      iii. a light chain sequence comprising SEQ ID NO: 3, SEQ ID NO: 5, and SEQ ID NO: 7, wherein Xaa in SEQ ID NO: 3 is Threonine or Alanine, and a heavy chain sequence comprising SEQ ID NO: 4, SEQ ID NO: 6, and SEQ ID NO: 8;
      iv. a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or
      v. a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

* * * * *

SEQUENCE LISTING

```
<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
```

<223> OTHER INFORMATION: adalimumab heavy chain variabe region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT

<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtaggga cagagtcacc      60 atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca cgccaagaa ctccctgtat    240

| | | |
|---|---|---|
| ctgcaaatga acagtctgag agctgaggat acggccgtat attactgtgc gaaagtctcg | | 300 |
| taccttagca ccgcgtcctc ccttgactat tggggccaag gtaccctggt caccgtctcg | | 360 |
| agt | | 363 |